(12) United States Patent
Boukhny

(10) Patent No.: US 7,967,799 B2
(45) Date of Patent: Jun. 28, 2011

(54) LIQUEFACTION HANDPIECE TIP

(75) Inventor: Mikhail Boukhny, Laguna Niguel, CA (US)

(73) Assignee: Alcon, Inc., Hunenburg (CH)

( * ) Notice: Subject to any disclaimer, the term of this patent is extended or adjusted under 35 U.S.C. 154(b) by 1391 days.

(21) Appl. No.: 11/082,084

(22) Filed: Mar. 16, 2005

(65) Prior Publication Data

US 2006/0212038 A1   Sep. 21, 2006

(51) Int. Cl.
A61M 1/00 (2006.01)
(52) U.S. Cl. .............................. 604/272; 604/19; 604/27
(58) Field of Classification Search .................... 604/19, 604/22, 27, 30, 35, 93.01, 158, 272, 273, 604/275; 607/107, 167
See application file for complete search history.

(56) References Cited

U.S. PATENT DOCUMENTS

| | | | |
|---|---|---|---|
| 1,493,450 A | 5/1924 | Richardson |
| 3,589,363 A | 6/1971 | Banko |
| 3,606,878 A | 9/1971 | Kellog |
| 3,818,913 A | 6/1974 | Wallach |
| 3,930,505 A | 1/1976 | Wallach |
| 3,994,297 A | 11/1976 | Kopf |
| 4,024,866 A | 5/1977 | Wallach |
| 4,169,984 A | 10/1979 | Parisi |
| 4,223,676 A | 9/1980 | Wuchinich et al. |
| 4,246,902 A | 1/1981 | Martinez |
| 4,249,899 A | 2/1981 | Davis |
| 4,265,618 A | 5/1981 | Herskovitz et al. |
| 4,301,802 A | 11/1981 | Poler |
| 4,493,694 A | 1/1985 | Wuchinich |
| 4,515,583 A | 5/1985 | Sorich |
| 4,517,977 A | 5/1985 | Frost |
| 4,570,632 A | 2/1986 | Woods |
| 4,577,629 A | 3/1986 | Martinez |
| 4,589,414 A | 5/1986 | Yshida |
| 4,589,415 A | 5/1986 | Haaga |
| 4,609,368 A | 9/1986 | Dotson, Jr. |
| 4,634,419 A | 1/1987 | Kreizman |
| 4,634,420 A | 1/1987 | Spinosa |
| 4,662,869 A | 5/1987 | Wright |
| 4,674,502 A | 6/1987 | Imonti |
| 4,689,040 A | 8/1987 | Thompson |
| 4,696,298 A | 9/1987 | Higgins et al. |
| 4,706,669 A | 11/1987 | Schlegel |
| 4,753,234 A | 6/1988 | Martinez |
| 4,869,715 A | 9/1989 | Sherburne |
| 4,909,249 A | 3/1990 | Akkas et al. |
| 4,911,161 A | 3/1990 | Schecter |
| 4,922,902 A | 5/1990 | Wuchinich et al. |
| 4,974,581 A | 12/1990 | Wiskell |

(Continued)

FOREIGN PATENT DOCUMENTS

EP    1388331 A1    2/2004

(Continued)

OTHER PUBLICATIONS

Fletcher, et al, "Pulsed Liquid Microjet for Microsurgery", Applied Physics Letters, vol. 78, No. 13 (Mar. 26, 2001).

Primary Examiner — Theodore J Stigell

(57) ABSTRACT

A surgical tip having a spacer or stand-off to keep the distal end of the tip from directly contacting delicate tissue, such as the posterior capsule. In addition, one or more bypass holes may be provided to help vent any excess pressure when the tip is near delicate tissue.

10 Claims, 1 Drawing Sheet

U.S. PATENT DOCUMENTS

| | | |
|---|---|---|
| 4,986,827 A | 1/1991 | Akkas |
| 4,989,583 A | 2/1991 | Hood |
| 4,989,588 A | 2/1991 | Kubota et al. |
| 5,019,035 A | 5/1991 | Missirlian et al. |
| 5,106,364 A | 4/1992 | Hayafuji et al. |
| 5,154,694 A | 10/1992 | Kelman |
| 5,226,910 A | 7/1993 | Kajiyama et al. |
| 5,250,065 A | 10/1993 | Clement et al. |
| 5,261,923 A | 11/1993 | Soares |
| 5,275,607 A | 1/1994 | Lo et al. |
| 5,284,472 A | 2/1994 | Sussman et al. |
| 5,285,795 A | 2/1994 | Ryan et al. |
| 5,322,504 A | 6/1994 | Doherty et al. |
| 5,359,996 A | 11/1994 | Hood |
| 5,423,330 A | 6/1995 | Lee |
| 5,554,155 A | 9/1996 | Awh et al. |
| 5,562,692 A | 10/1996 | Bair |
| 5,591,184 A | 1/1997 | McDonnell |
| 5,616,120 A | 4/1997 | Andrew |
| 5,624,392 A | 4/1997 | Saab |
| 5,624,393 A | 4/1997 | Diamond |
| 5,653,692 A | 8/1997 | Materson et al. |
| 5,669,923 A | 9/1997 | Gordon |
| 5,674,226 A | 10/1997 | Doherty et al. |
| 5,718,677 A | 2/1998 | Capetan et al. |
| 5,766,194 A | 6/1998 | Smith |
| 5,865,790 A | 2/1999 | Bair |
| 5,879,347 A | 3/1999 | Saadat |
| 5,885,243 A | 3/1999 | Capetan et al. |
| 5,891,095 A | 4/1999 | Eggers et al. |
| 5,947,988 A | 9/1999 | Smith |
| 5,989,212 A | 11/1999 | Sussman |
| 5,993,408 A | 11/1999 | Zaleski |
| 5,997,499 A | 12/1999 | Sussman |
| 6,039,715 A | 3/2000 | Mackool |
| 6,050,971 A * | 4/2000 | Garnier et al. ............ 604/43 |
| 6,110,162 A | 8/2000 | Sussman |
| 6,135,998 A | 10/2000 | Palanker |
| 6,139,571 A | 10/2000 | Fuller et al. |
| 6,146,380 A | 11/2000 | Racz et al. |
| 6,179,805 B1 | 1/2001 | Sussman |
| 6,196,989 B1 | 3/2001 | Padget et al. |
| 6,206,848 B1 | 3/2001 | Sussman |
| 6,287,274 B1 | 9/2001 | Sussman |
| 6,315,755 B1 | 11/2001 | Sussman |
| 6,331,171 B1 | 12/2001 | Cohen |
| 6,352,519 B1 | 3/2002 | Anis et al. |
| 6,398,759 B1 | 6/2002 | Sussman |
| 6,565,584 B1 | 5/2003 | Mathis et al. |
| 6,579,270 B2 | 6/2003 | Sussman et al. |
| 6,852,093 B1 | 2/2005 | Boukhny |
| 7,276,060 B2 | 10/2007 | Madden |
| 2002/0077585 A1 | 6/2002 | Sussman |
| 2004/0030349 A1 | 2/2004 | Boukhny |
| 2005/0256462 A1 | 11/2005 | Underwood |
| 2005/0277897 A1 | 12/2005 | Ghannoum et al. |
| 2005/0277898 A1 | 12/2005 | Dimalanta et al. |
| 2006/0047241 A1 | 3/2006 | Boukhny |
| 2006/0052741 A1 | 3/2006 | Boukhny et al. |
| 2006/0217740 A1 | 9/2006 | Ghannoum |
| 2006/0229632 A1 | 10/2006 | Madden et al. |
| 2007/0078378 A1 | 4/2007 | Kao et al. |
| 2007/0078470 A1 | 4/2007 | Tjia et al. |
| 2007/0260173 A1 | 11/2007 | Boukhny et al. |
| 2008/0167604 A1 | 7/2008 | Hong |

FOREIGN PATENT DOCUMENTS

| | | |
|---|---|---|
| EP | 1388331 B1 | 12/2004 |
| WO | WO 96/24314 | 8/1996 |
| WO | WO 01/30284 | 5/2001 |

* cited by examiner

U.S. Pat. No. 7,967,799 B2

LIQUEFACTION HANDPIECE TIP

BACKGROUND OF THE INVENTION

This invention relates generally to the field of cataract surgery and more particularly to a handpiece tip for practicing the liquefaction technique of cataract removal.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

A typical ultrasonic surgical device suitable for ophthalmic procedures consists of an ultrasonically driven handpiece, an attached cutting tip, and irrigating sleeve and an electronic control console. The handpiece assembly is attached to the control console by an electric cable and flexible tubes. Through the electric cable, the console varies the power level transmitted by the handpiece to the attached cutting tip and the flexible tubes supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve. Ultrasonic handpieces and cutting tips are more fully described in U.S. Pat. Nos. 3,589,363; 4,223,676; 4,246,902; 4,493,694; 4,515,583; 4,589,415; 4,609,368; 4,869,715; 4,922,902; 4,989,583; 5,154,694 and 5,359,996, the entire contents of which are incorporated herein by reference.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the cutting tip and horn bores and the aspiration line and into a collection device. The aspiration of emulsified tissue is aided by a saline flushing solution or irrigant that is injected into the surgical site through the small annular gap between the inside surface of the irrigating sleeve and the cutting tip.

Recently, a new cataract removal technique has been developed that involves the injection of hot (approximately 45° C. to 105° C.) water or saline to liquefy or gellate the hard lens nucleus, thereby making it possible to aspirate the liquefied lens from the eye. Aspiration is conducted concurrently with the injection of the heated solution and the injection of a relatively cool solution, thereby quickly cooling and removing the heated solution. This technique is more fully described in U.S. Pat. No. 5,616,120 (Andrew, et al.), the entire content of which is incorporated herein by reference. The apparatus disclosed in the publication, however, heats the solution separately from the surgical handpiece. Temperature control of the heated solution can be difficult because the fluid tubes feeding the handpiece typically are up to two meters long, and the heated solution can cool considerably as it travels down the length of the tube.

U.S. Pat. No. 5,885,243 (Capetan, et al.) discloses a handpiece having a separate pumping mechanism and resistive heating element. Such a structure adds unnecessary complexity to the handpiece.

U.S. Pat. Nos. 5,989,212, 5,997,499, 6,110,162, 6,179,805, 6,196,989, 6,206,848, 6,287,274, 6,315,755, 6,331,171 and 6,398,7596, the entire contents of which being incorporated herein by reference, all disclose various types of liquefaction handpieces and tips. These prior art tips do not allow the high pressure fluid stream to contact the cataractous material directly without leaving the tip and exposing the internal structures of the eye to the high pressure fluid stream.

Therefore, a need continues to exist for a liquefaction tip that allows the material being removed to be directly exposed to the high pressure fluid while preventing the remaining eye structures from being exposed to the high pressure fluid stream.

BRIEF SUMMARY OF THE INVENTION

The present invention improves upon the prior art by providing a surgical tip having a spacer or stand-off to keep the distal end of the tip from directly contacting delicate tissue, such as the posterior capsule. In addition, one or more bypass holes may be provided to help vent any excess pressure when the tip is near delicate tissue.

Accordingly, one objective of the present invention is to provide a liquefaction tip for delivering pulses of fluid.

Another objective of the present invention is to provide a liquefaction tip having a spacer or stand-off.

Another objective of the present invention is to provide a liquefaction tip having one or more bypass holes.

These and other advantages and objectives of the present invention will become apparent from the detailed description and claims that follow.

DETAILED DESCRIPTION OF THE INVENTION

Figure 1:
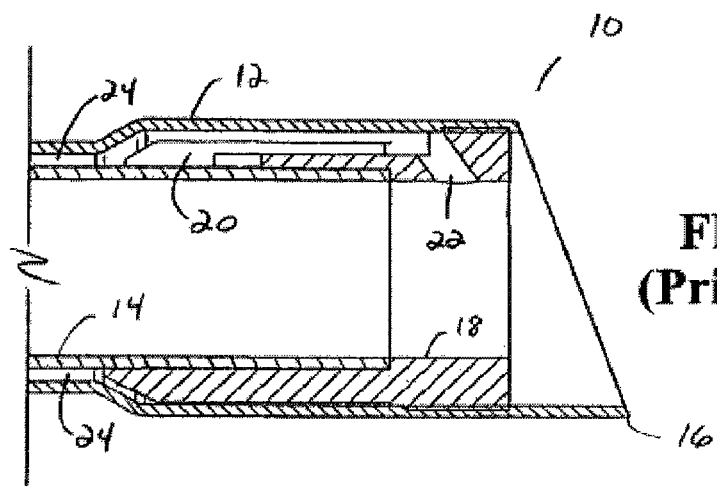
FIG. 1 is a partial cross-sectional view of a prior art liquefaction handpiece tip.

As best seen in FIG. 1, prior art liquefaction tip 10 generally consists of outer tube 12 surrounding and coaxial with inner tube 14. Distal tip 16 of outer tube 12 is flared or belled so as to allow nozzle 18 to be inserted between outer tube 12 and inner tube 14. Nozzle 18 contains fluid channel 20 that communicates with orifice 22. Nozzle 18 seals annular gap 24 between outer tube 12 and inner tube 14. Pressurized fluid flowing down annular gap 24 is forced into fluid channel 20, out orifice 22 and against inner tube 14 near distal tip 16. Such a construction prevents pressurized fluid from directly entering the eye, however, due to the straight configuration and angle of distal tip 16, lens material is restricted from entering outer tube 12 and being directly exposed to the fluid jet exiting orifice 22.

Figure 2:
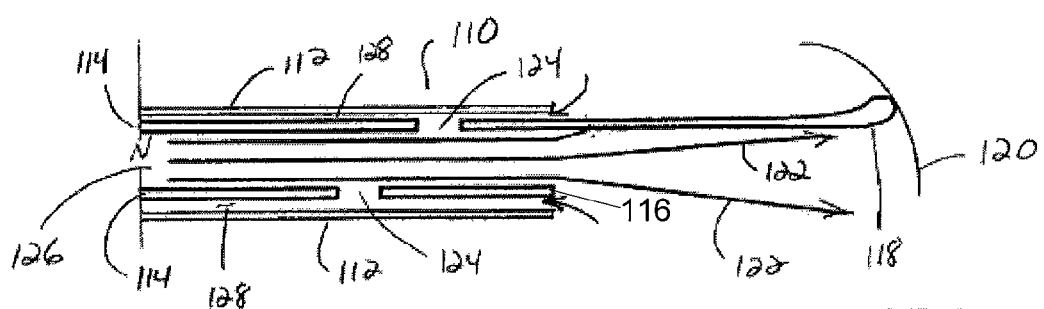
FIG. 2 is a partial cross-sectional view of the liquefaction handpiece tip of the present invention.

As best seen in FIG. 2, tip 110 of the present invention generally includes outer tube 112 surrounding and coaxial with inner tube 114. Distal tip 116 of inner tube 114 contains a spacer or stand-off 118 that prevents distal tip 116 from contacting tissue 120. Pulses of fluid 122 exiting distal tip 116 do not immediately contact tissue 120 but are allowed to dissipate or attenuate to some extent by the spacing provided by spacer 118 prior to contacting tissue 120. Such dissipation is especially advantageous around delicate eye tissue 120, such as the posterior capsule. Alternatively, or in addition, spacer 118 can be used as a "scrubber" for scrubbing or loosening lens epithelial cells ("LEC's") from the posterior capsule for consequent easier removal by irrigation.

Figure 3:
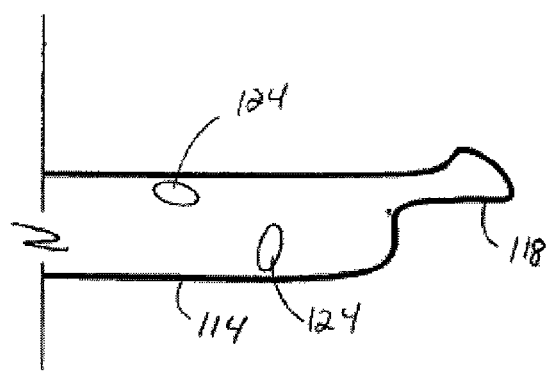
FIG. 3 is a partial elevational view of the liquefaction handpiece tip of the present invention.

In addition, as best seen in FIGS. 2 and 3, inner tube 114 may contain a plurality of bypass holes 124. Bypass holes 124 provide direct fluid communication between irrigating bore 126 of inner tube 114 and aspirating coaxial space 128 between inner tube 114 and outer tube 112. In operation, when distal tip 116 is unobstructed and fluid is allowed to flow freely out of bore 126, holes 124 have negligible effect on the strength of fluid pulses 122. When distal tip 116 is partially obstructed, such as when distal tip 116 is near tissue 120, this obstruction will cause an increase in backpressure within bore 126 during emission of fluid pulse 122. In such circumstances, excessive pressure is vented from bore 126 to coaxial space 128 (which is under vacuum), thereby dissipating the force of pulses 122 upon tissue 120.

This description is given for purposes of illustration and explanation. It will be apparent to those skilled in the relevant art that changes and modifications may be made to the invention described above without departing from its scope or spirit.

I claim:

1. A tip for a liquefaction handpiece, comprising:
   an inner tube coaxially mounted within an outer tube so as to form an annular gap between the inner tube and the outer tube, the inner tube having at least one bypass hole in a sidewall of the inner tube;
   wherein the inner tube has an irrigation bore and a non-beveled distal tip, comprising a distal tip opening, and a spacer formed on the distal tip and extending past the distal tip opening to provide a spacing between the distal tip opening and tissue such that pulses exiting the distal tip opening travel the spacing before contacting the tissue, the spacer including an enlarged, curved tip;
   wherein the inner tube is configured to direct pulses of fluid out of the distal tip opening;
   wherein the bypass hole is configured to vent excessive pressure from the irrigation bore to the annular gap when the distal tip opening becomes at least partially obstructed; and
   wherein the distal tip opening forms a plane that is perpendicular to a centerline of the inner tube and wherein the spacer extends outward from the plane of the distal tip opening.

2. The tip of claim 1, wherein the spacer is further configured to be used as a scrubber for scrubbing or loosening lens epithelial cells from a posterior capsule.

3. The tip of claim 1, wherein the pulses of fluid at least partially dissipate while traveling through the spacing between the distal tip and the tissue.

4. The tip of claim 1, wherein a portion of the spacer tip configured to contact tissue is rounded.

5. The tip of claim 1, wherein the spacing between the distal tip opening and an end of the spacer opposite the distal tip opening is greater than a diameter of the distal tip opening.

6. A tip for a liquefaction handpiece, comprising:
   an inner tube coaxially mounted within an outer tube so as to form an annular gap between the inner tube and the outer tube, the inner tube comprising:
   a non-beveled distal tip, comprising a distal tip opening, and a spacer formed on the distal tip and extending past the distal tip opening, the spacer including an enlarged, curved tip; and
   at least one bypass hole and an irrigation bore;
   wherein the inner tube is configured to direct pulses of fluid out of the distal tip opening and wherein the spacer is configured to provide a spacing between the distal tip and tissue such that pulses exiting the distal tip travel the spacing before contacting the tissue;
   wherein the bypass hole is configured to vent excessive pressure from the irrigation bore to the annular gap when the distal tip opening becomes at least partially obstructed; and
   wherein the distal tip opening forms a plane that is perpendicular to a centerline of the inner tube and wherein the spacer extends perpendicular to the plane of the distal tip opening.

7. The tip of claim 6, wherein the spacer is further configured to be used as a scrubber for scrubbing or loosening lens epithelial cells from a posterior capsule.

8. The tip of claim 6, wherein the pulses of fluid at least partially dissipate while traveling through the spacing between the distal tip and the tissue.

9. The tip of claim 6, wherein a portion of the spacer tip configured to contact tissue is rounded.

10. The tip of claim 6, wherein the spacing between the distal tip opening and an end of the spacer opposite the distal tip opening is greater than a diameter of the distal tip opening.

* * * * *